(12) United States Patent
Lunn

(10) Patent No.: US 6,489,355 B2
(45) Date of Patent: *Dec. 3, 2002

(54) METHODS OF INHIBITING THE EFFECTS OF AMYLOIDOGENIC PROTEINS

(75) Inventor: William H. W. Lunn, Indianapolis, IN (US)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/160,379

(22) Filed: Dec. 1, 1993

(65) Prior Publication Data

US 2001/0051368 A1 Dec. 13, 2001

(51) Int. Cl.⁷ .............................................. A61K 31/38

(52) U.S. Cl. ....................... 514/443; 514/324; 514/408; 514/422

(58) Field of Search ................. 514/443, 324, 514/408, 422

(56) References Cited

U.S. PATENT DOCUMENTS

| | | | |
|---|---|---|---|
| 4,133,814 A | 1/1979 | Jones et al. | |
| 4,380,635 A | 4/1983 | Peters | |
| 4,418,068 A | 11/1983 | Jones | |
| 4,960,815 A | * 10/1990 | Moos | 424/1.1 |
| 5,075,321 A | 12/1991 | Schreiber | |
| 5,081,304 A | * 1/1992 | Moos | 564/427 |
| 5,098,925 A | * 3/1992 | Bare | 514/409 |
| 5,145,892 A | * 9/1992 | Driedgor et al. | 514/63 |
| 5,162,364 A | * 11/1992 | Debaert et al. | 514/438 |
| 5,175,164 A | * 12/1992 | Bagley et al. | 514/259 |
| 5,177,074 A | * 1/1993 | Allen et al. | 514/234.2 |
| 5,189,041 A | * 2/1993 | Berger et al. | 514/288 |
| 5,192,220 A | * 3/1993 | Clerk et al. | 514/305 |
| 5,198,438 A | * 3/1993 | Allon et al. | 514/235.8 |
| 5,214,063 A | * 5/1993 | Debaert et al. | 514/394 |
| 5,252,524 A | * 10/1993 | Allen et al. | 514/259 |
| 5,278,166 A | * 1/1994 | Debaert et al. | 514/259 |
| 5,288,249 A | * 2/1994 | Meyer et al. | 514/414 |
| 5,393,763 A | * 2/1995 | Black et al. | 514/333 |
| 5,464,845 A | * 11/1995 | Black et al. | 514/326 |
| 5,552,415 A | * 9/1996 | May | 514/324 |
| 5,652,259 A | * 7/1997 | May | 514/422 |
| 5,686,476 A | * 11/1997 | May | 514/324 |

FOREIGN PATENT DOCUMENTS

| | | |
|---|---|---|
| JP | WO93/10113 | 5/1993 |
| WO | WO93/1074 | 6/1993 |

OTHER PUBLICATIONS

Schneider LS, Psychopharmacol Bull 29:501–24 (1993).*
Haan et al, Dementia 5:210–3 (1994).*
U.S. patent application Ser. No. 07/920,933, Black et al., filed Jul. 28, 1992.
U.S. patent application Ser. No. 07/995,222, Black et al., filed Dec. 22, 1992.
U.S. patent application Ser. No. 08/035,121, Black et al., filed Mar. 19, 1993.
U.S. patent application Ser. No. 08/082,218, Cullinan, filed Jun. 24, 1993.
U.S. patent application Ser. No. 08/096,480, Hock, filed Jul. 22, 1993.
U.S. patent application Ser. No. 08/112,012, Dodge et al., filed Aug. 15, 1993.
U.S. patent application Ser. No. 08/111,796, Dodge et al., filed Aug. 25, 1993.
U.S. patent application Ser. No. 08/081,610, Yang, filed Jun.

(List continued on next page.)

Primary Examiner—Irene Marx
(74) Attorney, Agent, or Firm—William R. Boudreaux; James J. Sales

(57) ABSTRACT

This invention encompasses methods for the inhibition of a physiological disorder associated with amyloidogenic proteins, which method comprises administering to a human in need thereof an effective amount of a compound of Formula I

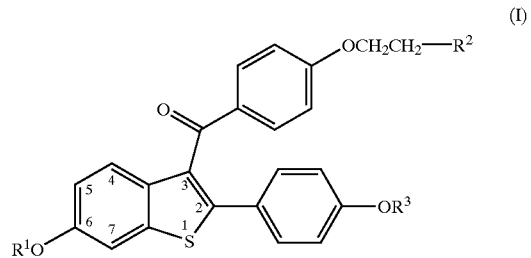

wherein $R^1$ and $R^3$ are independently hydrogen,

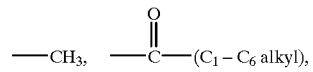

or 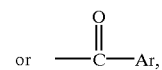

wherein Ar is optionally substituted phenyl;
$R^2$ is selected from the group consisting of pyrrolidine, hexamthylenemino, and piperidino; or a pharmaceutically acceptable salt of solvate thereof.

1 Claim, No Drawings

OTHER PUBLICATIONS 21, 1993.

Draper et al., "Effects of Raloxifene (LY139481 HC1) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Vitro Metabolism of Raloxifene", Am. Soc. Bone & Res., Tampa, Sep. 18–22, 1993.

Glasebrook et al., "Multiple Binding Sites for the Anti–estrogen Raloxifene", Am Soc. Bone & Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene on Anti–Estrogen, Simulates the Effects of Estrogen in Inhibiting Bone Resorption Through TGFB–3 Expression in Bone;".Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endocrine Soceity, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular Endocrinology, 22:1981, 95–103.

Black et al., "Evidence for Biological Action of the Antiestrogens LY117018 and Tamoxifen by Different Mechanisms," Endocrinology 109;1981, 987–989.

Black, L.J. "Biological Actions and Binding Properties of a New Estrogen Antagosist LY117018," In: Homone Antagonists, 129–82, 1982 (M.K. Agarwal ed.) Walter de Gruyter and Co., Berlin New York.

Black et al., LY156758: A Unique Antiestrogen Displaying High Affinity for Estrogen Receptors, Negligible Activity and Near–Total Estrogen Antagonism in Vivo. Presented at the fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl) ethoxyl]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

"Women on estrogen appear at less risk of Alzheimer's", Indianapolis Star, p. 1, col. 1, Nov. 10, 1993.

* cited by examiner

METHODS OF INHIBITING THE EFFECTS OF AMYLOIDOGENIC PROTEINS

BACKGROUND OF THE INVENTION

Alzheimer's Disease (AD) is a degenerative brain disorder characterized clinically by progressive loss of memory, cognition, reasoning, judgment and emotional stability that gradually leads to profound mental deterioration and ultimately death. AD is a common cause of progressive mental failure (dementia) in aged humans and is believed to represent the fourth most common medical cause of death in the United States. AD has been observed in varied races and ethnic groups worldwide and presents a major present and future public health problem. The disease is currently estimated to affect about two to three million individuals in the United States alone. To date, AD has proven to be incurable.

The brains of individuals with AD exhibit neuronal degeneration and characteristic lesions variously referred to as amyloidogenic plaques, vascular amyloid angiopathy, and neurofibrillary tangles. Large numbers of these lesions, particularly amyloidogenic plaques and neurofibrillary tangles, are generally found in several areas of the human brain important for memory and cognitive function in patients with AD. Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome) and Hereditary Cerebral Hemorrhage with Amyloidosis of the Dutch-Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

Several lines of evidence indicate that progressive cerebral deposition of particular amyloidogenic proteins, β-amyloid proteins, (βAP), play a seminal role in the pathogenesis of AD and can precede cognitive symptoms by years or decades. See, Selkoe, (1991) Neuron 6:487. Recently, it has been shown that βAP is released from neuronal cells grown in culture and is present in cerebrospinal fluid (CSF) of both normal individuals and AD patients. See, Seubert et al., (1992) Nature 359:325–327.

In addition to Alzheimer's Disease and other conditions associated with the amyloidogenic peptides βAP, there exist conditions associated with other amyloidogenic peptides which are structurally similar to βAP but which share no sequence homology with βAP. Recent studies have demonstrated the functional interchangeability of many of these amyloidogenic peptides with regard to neurotoxicity. P. C. May, et al., *Journal of Neurochemistry*, (December 1993); co-pending U.S. patent application Ser. No. 08/109,782, filed Aug. 19, 1993 (Docket X-9342).

Despite the progress that has been made in understanding the underlying mechanisms of AD and other amyloidogenic protein related diseases, there remains a need to develop compositions and methods for treatment of these diseases. Treatment methods could advantageously be based on drugs which are capable of inhibiting the generation or effect of amyloidogenic proteins.

SUMMARY OF THE INVENTION

This invention encompasses methods for the inhibition of a physiological disorder associated with amyloidogenic proteins, which method comprises administering to a human in need thereof an effective amount of a compound of formula I

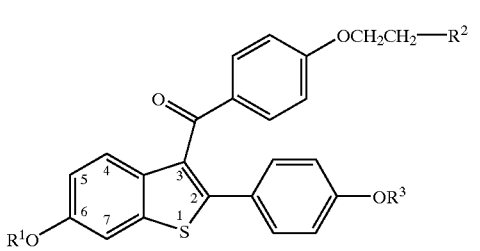

wherein $R^1$ and $R^3$ are independently hydrogen,

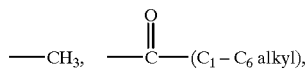

or

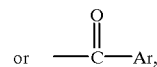

wherein Ar is optionally substituted phenyl;
$R^2$ is selected from the group consisting of pyrrolidino, hexamethylenemino, and piperidino; or a pharmaceutically acceptable salt of solvate thereof.

The present invention also provides a method of inhibiting amyloidogenic protein production comprising administering to a human in need thereof an effective amount of a compound of formula 1.

The present invention also provides a method of inhibiting the deposition of amyloid plaque comprising administering to a human in need thereof an effective amount of a compound of formula 1.

The present invention also provides a method of inhibiting Alzheimer's Disease (AD) comprising administering to a human in need thereof an effective amount of a compound of formula 1.

DETAILED DESCRIPTION OF THE INVENTION

The current invention concerns the discovery that a select group of benzothiophenes, those of formula I, are useful for inhibiting the effects of amyloidogenic proteins, and in particular the compounds inhibit amyloidogenic protein formation. The invention encompasses uses practiced by administering to a human in need thereof a dose of a compound of formula 1 or a pharmaceutically acceptable salt or solvate thereof effective to inhibit a physiological disorder associated with amyloidogenic proteins, and preferably β-amyloid proteins.

The term "inhibit" includes its generally accepted meaning which includes prohibiting, preventing, restraining, and slowing, stopping, or reversing progression, severity, or a resultant symptom. As such, the methods include both therapeutic and prophylactic administration.

The term "physiological disorder associated with an amyloidogenic protein" includes diseases related to the innapropriate or undesirable deposition, such as in the brain, liver, kidney or other organ, of at least one amyloidogenic protein, and as such includes AD (includes familial AD), Down's Syndrome, HCHWA-D, advanced aging of the brain and the like.

The term "effective amount" means the amount of compound necessary to inhibit physiological effects or disorders associated with an amyloidogenic protein, or inhibit amyloidogenic production or deposition, or inhibit Alzheimers disease, as the case may be.

The term "amyloidogenic protein" as used herein refers to those peptides which have the ability to self-associate into higher ordered aggregates and eventually assemble into an amyloid plaque. The preferred target amyloidogenic proteins are β-amyloid proteins.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established and analogous procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, alkylated, and deprotected to form the formula I compounds. Examples of the preparation of such compounds are provided in the U.S. patents discussed above, and in the examples in this application. Optionally substituted phenyl includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

Included in this invention is the compound raloxifene, below:

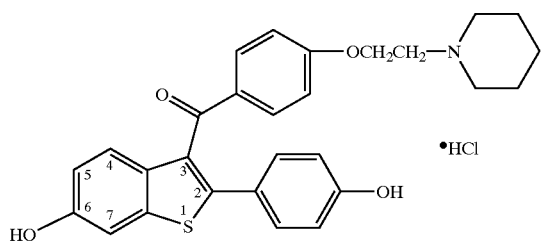

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferable salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides and carbonates, as well as aliphatic and aromatic amines, aliphatic diamines and hydroxy alkylamines. Bases especially useful in the preparation of addition salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

Compounds of Formula I can be administered for prophylactic and/or therapeutic treatment of diseases related to the deposition of one or more amyloidogenic proteins such as Alzheimer's disease, Down's syndrome, and advanced aging of the brain. In therapeutic applications, the compounds are administered to a host already suffering from a disease. The compounds are administered in an amount sufficient to inhibit physiological effects or disorders related to amyloidogenic protein, especially β-amyloid proteins.

For prophylactic applications, the compounds of formula I are administered to a host susceptible to an amyloidogenic protein related disease, preferably Alzheimer's disease, but not already suffering from such disease. Such hosts may be identified by genetic screening and clinical analysis, as described in the medical literature. see e.g., Goate, *Nature*, 349:704–706 (1991). The compounds will inhibit the amyloid protein plaque at a symptomatically early stage, preferably preventing even the initial stages of the amyloidogenic protein related disease. A preferred group for receiving compounds of the invention, either for prophylactic or therapeutic reasons, are post-menopausal women.

The particular dosage of a compound of formula I according to this invention will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need of treatment from once to about three times each day, or more often as needed, for a period of time sufficient to inhibit the disease or disorder.

Frequently, it will be desirable or necessary to introduce the pharmaceutical compositions directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid-soluble drugs. Latentiation is generally achieved through blocking of the hydroxyl, carboxyl, and primary amine groups present on the drug to render the drug more lipid soluble and amenable to transportation across the blood-brain barrier. Alternatively, the delivery of hydrophilic drugs can be enhanced by intra-arterial infusion of hypertonic solutions which can transiently open the blood-brain barrier.

It is usually preferred to administer a compound of formula I in the form of an acid addition salt, as is customary in the administration of pharmaceuticals bearing a basic group, such as the piperidino ring. For such purposes the following dosage forms are available.

Formulations

In the formulations which follow, "Active ingredient" means a compound of formula I.

Formulation 1: Gelatin Capsules
Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of the compound raloxifene that have been made include those shown below:

Formulation 2: Raloxifene capsule

| Ingredient | Quantity (mg/capsule) |
|---|---|
| Raloxifene | 1 |
| Starch, NF | 112 |
| Starch flowable powder | 225.3 |
| Silicone fluid 350 centistokes | 1.7 |

Formulation 3: Raloxifene capsule

| Ingredient | Quantity (mg/capsule) |
|---|---|
| Raloxifene | 5 |
| Starch, NF | 108 |
| Starch flowable powder | 225.3 |
| Silicone fluid 350 centistokes | 1.7 |

Formulation 4: Raloxifene capsule

| Ingredient | Quantity (mg/capsule) |
|---|---|
| Raloxifene | 10 |
| Starch, NF | 103 |
| Starch flowable powder | 225.3 |
| Silicone fluid 350 centistokes | 1.7 |

Formulation 5: Raloxifene capsule

| Ingredient | Quantity (mg/capsule) |
|---|---|
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
|---|---|
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

| Formulation 7: Tablets | |
|---|---|
| Ingredient | Quantity (mg/tablet) |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

| Formulation 8: Suspensions | |
|---|---|
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Assays
Experimental Design

For Assay 1 through 3, the following experimental design is provided.

Amylins may be purchased from Bachem, Inc. (Torrance, Calif.), Peninsula Laboratories, Inc. (Belmont, Calif.), Sigma Chemicals (St. Louis, Mo.) or may be synthesized as described infra. Amyloid-β(1-40) [Lot # ZK052] and reverse β-amyloid peptide(40-1) [Lot # ZX299] may be purchased from Bachem, Inc. $β_2$-microglobulin may be purchased from Sigma Chemicals (St. Louis, Mo.).

Stock solutions of peptides (1 mM) are freshly prepared in pyrogen-free sterile water and diluted to the indicated concentrations in defined culture media. Rat hippocampal cultures (10–14 days in vitro) are treated with peptides or vehicle for four days. The viability of the rat cortical cultures is visually assessed by phase contrast microscopy and quantified by measuring lactate dehydrogenase (LDH) released into the culture media.

Human cortical cultures (19–22 days in vitro) are treated with peptides or vehicle for three days. Cell viability is visually assessed by phase contrast microscopy and quantified by measuring the reduction of the tetrazolium salt XTT.

It is understood by those in the art that cell viability, and consequently, toxicity can be measured using other techniques such as monitoring calcium levels. The LDH and XTT techniques as well as the calcium level monitoring assay are described infra.

Assay 1

Neurotoxicity Assay Measuring Calcium Levels

An aliquot of ED 18 cortical cells are seeded into polyethylenimine-coated tissue culture dishes for 3–5 days in vitro before treatment with a 25 μM solution of β-amyloid peptide, either freshly dissolved (predominantly random coil conformation) or aged (7 days, predominantly β-sheet conformation). This neurotoxicity assay is conducted in chemically-defined HEPES-buffered DMEM supplemented with fetal calf serum.

After a two day incubation with the β-amyloid peptide, the elevation of cytosolic calcium ($Ca^{+2}$) concentrations after a glutamate pulse are determined using a fluorescent calcium dye. J. Wahl, et al., *Journal of Neurochemistry,* 53:1316 (1989). The elevation of intracellular $Ca^{+2}$ levels compromises cell integrity. The above is run again, however with a compound of the invention. Activity of the compound is illustrated by a decrease of intracellular $Ca^{+2}$ levels as compared to the first run.

Assay 2

Neurotoxicity Assay Measuring XTT

An aliquot of ED 18 cortical cells is seeded into polyethylenimine-coated tissue culture dishes for 3–5 days in vitro before treatment with a 25 μM solution of β-amyloid peptide, either freshly dissolved (predominantly random coil conformation) or aged (7 days, predominantly β-sheet conformation). This assay is conducted in chemically-defined HEPES-buffered DMEM supplemented with fetal calf serum.

These cells are incubated for 3 to 5 days in vitro before treatment with a 25 μM solution of β-amyloid peptide, either freshly dissolved (predominantly random coil conformation) or aged (7 days, predominantly β-sheet conformation). After two days of incubation, cell viability is assessed by measuring the reduction of the tetrazolium salt XTT [2,3-bis(2-methoxy-4-nitro-5-sulfophenyl)-2H-tetrazolium-5-carboxanilide inner salt] as described by N. Roehm, et al., *Journal of Immunological Methods,* 142:257 (1992). The above is run again, however with a compound of the invention. Activity of the compound is illustrated by an increase of cell viability as compared to the first run.

Assay3

Neurotoxicity Assay Measuring LDH

Lactate dehydrogenase (LDH) is measured in 20 μl aliquots of conditioned defined-DMEM using a standard 340 nm kinetic LDH assay (Sigma Catalog Number #228-20) in a 96 well format. Assays are performed at 37° C. in a PC-driven EL340 Microplate Biokinetics plate reader (Bio-Tek Instruments) using Delta Soft II software (v. 3.30B, BioMetallics, Inc.) for data analysis. Quality control standards containing normal and elevated levels of serum LDH (for example, Sigma Enzyme Controls 2N and 2E) are run with every assay. A compound of the invention is added in varying concentrations to a portion of the wells. Results are expressed as units of LDH/L where 1 unit is defined as the amount of enzyme that will catalyze the formation of 1 micromole of nicotinamide adenine dinucleotide per minute under conditions of the assay. Activity is indicated by a decrease in the neurotoxicity indicator levels as compared to control.

Assay 4

Cells infected with VV:99 or VV:42 which are capable of forming amyloid deposits, (as described in WO 91/04339, published Apr. 4, 1991, incorporated by reference herein), are plated in a 96-well microtiter plate. To make the appropriate dilutions and additions, an automated pipetter is used to introduce a compound of formula 1 to be tested to the cells. A range of concentrations of the compound is incubated in a tissue culture incubator (or preincubated) with the cells at 37° C. for a predetermined time period, or alternatively, for 3 to 72 hours.

Following incubation, the culture media is removed, and the cells are prepared for preamyloid measurement as follows. The cells are fixed for immunocytochemical staining with amyloid antibodies. The primary antibodies are introduced followed by incubation with labeled, secondary antiantibodies and the level of binding between the primary and secondary antibodies is measured using an ELISA plate reader to record the optical density of the labeled antibody. A smaller optical density reading as compared to a control sample of cells grown in the absence of the test drug is indicative of that drug's ability to inhibit amyloid deposition. This procedure may be modified to permit detection of preamyloid dissolution using a correlative enzyme marker. Activity of the compounds of Formula 1 is illustrated by a decrease in the preamyloid measurement as compared to control.

Assay 5

Five to fifty women are selected for the clinical study. The women are post-menopausal, i.e., have ceased menstruating for between 6 and 12 months prior to the study's initiation, have been diagnosed with early stage Alzheimer's Disease (AD), are expected to have worsening symptoms of AD within the study period, but are in good general health otherwise. The study has a placebo control group, i.e., the women are divided into two groups, one of which receives the active agent of this invention and the other receives a placebo. The patients are benchmarked as to memory, cognition, reasoning, and other symptoms associated with AD. Women in the test group receive between 50–200 mg of the active agent per day by the oral route. They continue this therapy for 6–36 months. Accurate records are kept as to the benchmarked symptoms in both groups and at the end of the study these results are compared. The results are compared both between members of each group and also the results for each patient are compared to the symptoms reported by each patient before the study began. Activity of the test drug is illustrated by an inhibition of any one or more of the symptoms of AD in the patients taking the test drug.

Utility of the compounds of formula I is evidenced by activity in at least one of the above assays.

I claim:

1. A method of inhibiting Alzheimer's Disease comprising administering to a post-menopausal woman diagnosed with Alzheimer's Disease an effective amount of a compound of the formula

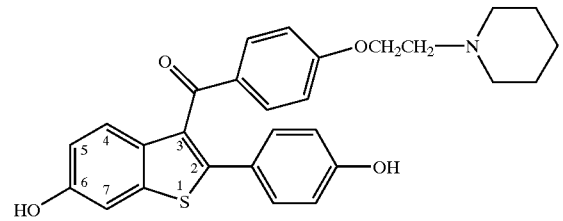

or its hydrochloride salt.

* * * * *